United States Patent [19]

Asano et al.

[11] Patent Number: 4,885,290

[45] Date of Patent: Dec. 5, 1989

[54] IMMUNOREGULATOR COMPRISING A DERIVATIVE OF ESTRADIOL

[75] Inventors: Kiro Asano, Kukizaki; Tadahiro Matsudaira, Tokyo; Humio Tamura, Kukizaki; Toichi Suzuki, Tokyo; Hisayuki Wada, Matsudo, all of Japan

[73] Assignee: Kureha Kagaku Kogyo Kabushiki Kaisha, Tokyo, Japan

[21] Appl. No.: 113,911

[22] Filed: Oct. 29, 1987

[30] Foreign Application Priority Data

Nov. 12, 1986 [JP] Japan .................. 61-268940

[51] Int. Cl.$^4$ ............................. A61K 31/56
[52] U.S. Cl. .................. 514/182; 514/855; 514/960; 514/961
[58] Field of Search ............ 514/182, 855, 177, 178, 514/179, 960, 961

[56] References Cited

U.S. PATENT DOCUMENTS

| | | | |
|---|---|---|---|
| 3,639,599 | 2/1972 | Mehrhof et al. | 514/170 |
| 4,029,778 | 6/1977 | Fex et al. | |
| 4,096,254 | 6/1978 | Benson et al. | 514/177 |
| 4,217,345 | 8/1980 | Shinohara et al. | 514/885 |
| 4,261,910 | 4/1982 | Asano et al. | |
| 4,332,797 | 6/1982 | Asano et al. | |
| 4,378,356 | 3/1983 | Jager | 514/170 |
| 4,395,408 | 7/1983 | Torelli et al. | 514/885 |
| 4,581,372 | 10/1983 | Koda et al. | 514/451 |
| 4,701,450 | 10/1987 | Kelder et al. | 514/182 |
| 4,719,228 | 1/1988 | Rawlins | 514/960 |

FOREIGN PATENT DOCUMENTS

| | | |
|---|---|---|
| 2702509 | 1/1977 | Fed. Rep. of Germany. |
| 2932607 | 8/1979 | Fed. Rep. of Germany. |
| 1050919 | 3/1986 | Japan .................. 514/182 |
| 1558472 | 1/1976 | United Kingdom. |
| 1527161 | 2/1976 | United Kingdom. |
| 2028335 | 8/1979 | United Kingdom. |

OTHER PUBLICATIONS

10th *International Congress of Chemotherapy*, Abstracts, Sep. 18–23, 1977.
Nishinihon J. Urol., 47(1), pp. 29–32 (1985), "Bone Marrow Suppression by an Estradiol–Chlorambucil Conjugate", Kimio Fujita et al.
*Vop Onkol.*, 14, p. 61 (1968), Referenced in Chem. Abst., 70, (1969), Section 3472b, "Antitumor Action of p-[bis(-2-chlorethyl)amio]-phenylacetic esters with Estrogens", Larionov et al.
*J. Med. Chem.*, 12, (1969), pp. 810–818, "The Effects of Some Steroidal Alkylating Agents on Experimental Animal Mammary Tumor and Leukemia Systems", Monroe E. Wall et al.
*J. Med. Chem.*, 15, (11), (1972), pp. 1158–1161, "Antitumor and Antileukemic Effects of Some Steroids and Other Biologically Interesting Compounds Containing an Alkylating Agent", F. I. Carroll et al.

*Primary Examiner*—H. M. S. Sneed
*Assistant Examiner*—J. Saba
*Attorney, Agent, or Firm*—Oblon, Spivak, McClelland, Maier & Neustadt

[57] ABSTRACT

Disclosed herein is an immunoregulator comprising a derivative of estradiol represented by the formula (I), which immunoregulator has a small influence to the non-specific immunoreactions in general and gives a specific influence to the immunoreactions against an isoantibody.

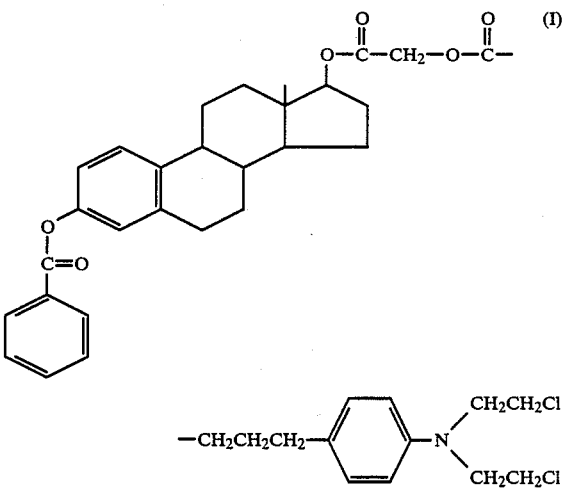

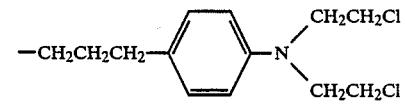

7 Claims, No Drawings

IMMUNOREGULATOR COMPRISING A DERIVATIVE OF ESTRADIOL

BACKGROUND OF THE INVENTION

The present invention relates to an immunoregulator comprising a derivative of estradiol, which is represented by the following formula (I):

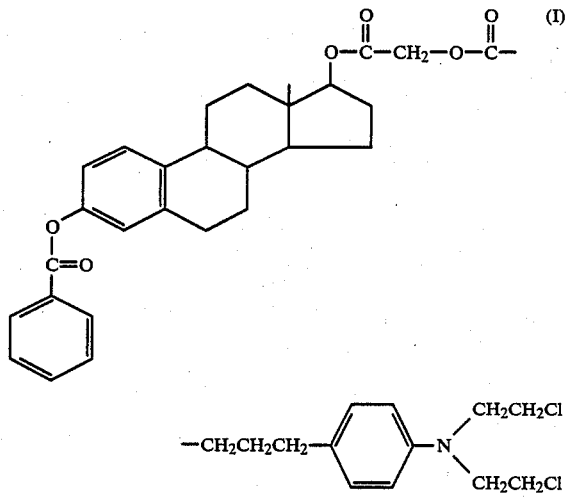

The immunoregulator according to the present invention has a small influence to the non-specific immunoreactions and is active specifically to the immunoreaction against an isoantibody.

The immunosuppressor such as cyclophosphamide, azathiopurine, prednisolone, cyclosporin A, etc., which has hitherto been used as the immunoregulator for suppressing the foreign body rejection reaction, so-called the immunorejection which is a problem in an organ transplantation, even suppresses the nonspecific immunoreaction which has no relationship with the immunorejection. Accordingly, it has a strong side effect that the immunological competence of a patient is reduced and a severe infectious disease is caused, and there are various restrictions in its clinical use. Consequently, the development of a substance which specifically suppresses the immunoreaction against the isoantibody controlling the immunorejection which is a problem in an organ transplantation, has been desired.

As a result of the present inventors' earnest studies for obtaining an immunoregulator which does not unnecessarily suppress the immunoreaction, specifically suppresses the immunoreactions in the necessary range, is small in toxicity and has an excellent effect, it has been found by the present inventors that an immunoregulator containing the derivative of estradiol represented by the above formula (I) is effective in the above object, and on the basis of their finding, the present invention have been completed.

SUMMARY OF THE INVENTION

The object of the present invention is to provide an immunoregulator containing the derivative of estradiol, which is represented by the following formula (I):

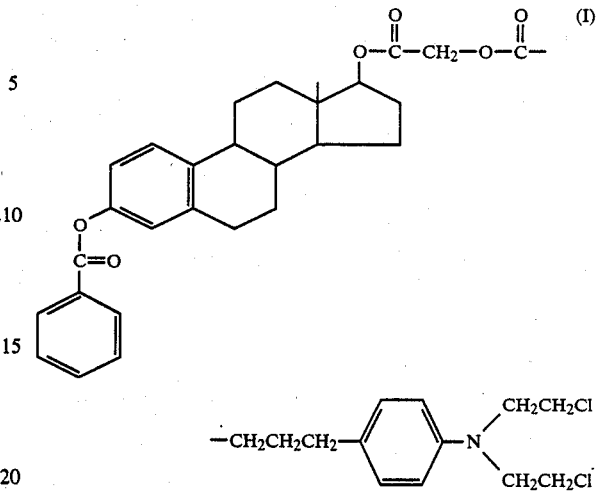

Further, the object of the present invention is to provide an immunoregulator which has small side effect and is excellent in efficacy.

Still more, the object of the present invention is to provide an immunoregulator which does not nonspecifically control the immunity but is specifically active to the immunoreaction against an isoantibody.

Still further, the object of the present invention is to provide a medicine which is effective in graft versus host disease following bone marrow transplantation, in the suppression of the immunorejection in the transplant operation of bone marrow, kidney, skin, heart, etc. and in the treatment of various renal diseases, thyroid diseases, chronic articular rheumatism, thrombocytopenia, systemic lupus erythematosus, severe myasthenia, hepatic diseases, autoimmune diseases, polymyositis, etc.

DETAILED DESCRIPTION OF THE INVENTION

The present invention relates to the use of the derivative of estradiol represented by the following formula (I) as an immunoregulator:

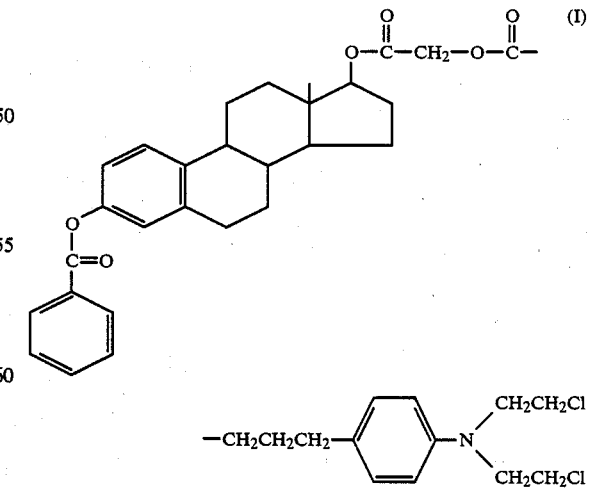

As is clearly seen in the above formula (I), the derivative of estradiol is a double ester type wherein a benzoyl group has been bound to the OH group at 3-position of estradiol and a chlorambucil (known as an anti-cancer drug) to the OH group at 17-position of estradiol via a binding group of a certain length.

In order to determine its $LD_{50}$ value, the derivative of estradiol (hereinafter referred to as the present substance) is orally administered to rats, but even at the maximum administable dose of 6000 mg/kg, no death case was observed. On the other hand, the value of acute oral $LD_{50}$ of chlorambucil to male rat is 98 mg/kg and that to female rat is 76 mg/kg. Namely, it will be well understood that how safe is the present substance.

By the way, the process for producing the present substance and the details of the acute toxicity thereof have been disclosed in British Pat. No. 2,028,335.

The present substance is 3-benzoyloxy-1,3,5(10)-estratriene-17-[4-{p-(bis(2-chloroethyl)amino)phenyl}butanoyloxy]acetate represented by the following formula (I):

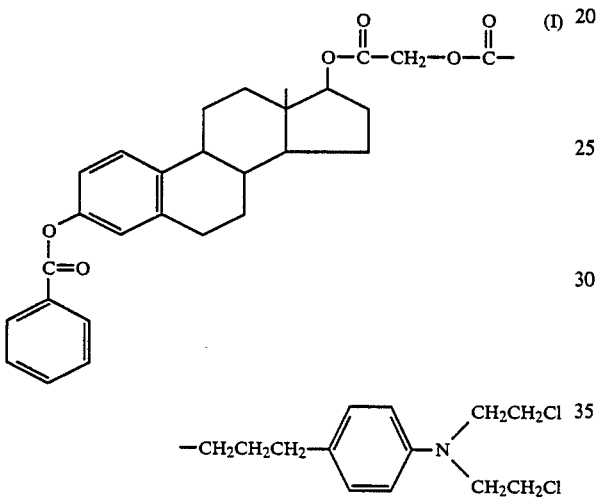

The present substance may also be called as estra-1,3,5(10)-triene-3,17-diol,3-benzoate,17-[4-{4-(bis(2-chloroethyl)amino)phenyl}-1-oxobutoxy]acetate.

Moreover, the estradiol may be estradiol-17β, estradiol-17α or a mixture thereof, however, the present substance using estradiol-17β is preferable.

The immunoregulator mentioned in the present invention means the medicine having an immunoregulating activity and simultaneously also an immunosuppressive activity. Accordingly, the present substance is effective in the prevention and treatment of the various diseases which originate in the immunoreaction. For instance, the present substance is used in treating the following diseases such as immunorejection in the transplantation of bone marrow, kidney, skin, heart, etc., various renal diseases, thyroid diseases, chronic articular rheumatism, thrombocytopenia, systemic lupus erythematosus, severe myasthenia, hepatic diseases, autoimmune diseases, polymyositis, etc.

The major appearance of the toxicity of the present substance is due to the presence of a minute amount of 3-benzoyloxy-estradiol, which is a metabolite of the present substance and do certain influence to genital organs, the reduction of pregnancy rate and the abortion.

Further, as the action of chlorambucil which is also a metabolite of the present substance, the reduction of a number of lymphocytes is observed at a high dosage of the present substance, however, the typical toxicity of chlorambucil such as hypoplasia of bone marrow, hepatic failure, teratogenesis, mutagenesis, etc. has not been observed in animals administered with the present substance.

On the other hand, although chlorambucil has the carcinogenicity on lymphoma, lung cancer, skin cancer, etc., when the present substance is administered for a long time to rats, any significant increase of the rate of carcinogenesis has not been recognized.

The present substance is an extremely unique immunosuppressor which selectively suppresses the immunoreaction specific to an isoantigen as compared to the influence to the non-specific immunoreactions.

The non-specific immunoreactions were studied by PHA reaction and the specific immunoreaction to an isoantigen were studies by MLC (mixed lymphocyte culture) reaction.

The present substance is provided as the unit form administration as the medicine, for instance, tablet, granule, powder, capsule etc. for oral administration, and the medicinal composition may contain a binder, an excipient, a demulcent, a lubricant, a surfactant and a desintegrator. The liquid medicinal composition for oral administration of the present substance can take the form of an aqueous- or oily suspension, a solution, a syrup or a shaken mixture. In case of a suppository, an oilphilic- or hydrophilic base material may be combined with a stabilizer, a decomposer, a pigment, etc. Into the injection liquid, a solubilizer, a nutritive aliment, a stabilizer, a surfactant, etc. may be admixed. From the viewpoint of the light-stability and the ease of taking, the capsulated present substance is preferable.

As an example of these carriers, the following substances can be mentioned:

Lactose, sucrose, sorbitol, mannitol, potato starch, corn starch, amylopectin, other various starches, crystalline cellulose, derivatives of cellulose (for instance, carboxymethyl cellulose and methylcellulose), gelatin, magnesium stearate, polyvinyl alcohol, sodium alginate, calcium stearate, polyethylene glycol, propylene glycol, wax, gum arabic, talc, titanium dioxide, light silicic anhydride, vegetable oil such as olive oil, peanut oil, sesame oil, etc., paraffin oil, cacao butter, alcohols (for instance, ethanol and benzyl alcohol), physiological saline solution, sterilized water, glycerol, vaseline, polysorbate, sodium chloride, potassium chloride, etc.

The medicinal composition prepared is administered by various routes such as oral, percutaneous, intramuscular, intraperitoneal, intravenous, intrarectal and topical.

Although the dose of the present substance depends on the mode of administration and the extent of the treatment, in the case of oral administration, the daily dose for adult is about 0.1 mg/kg to 50 mg/kg, preferably 0.5 mg/kg to 18 mg/kg.

The present invention will be explaines in detail while referring to the following non-limitative Examples, and as far as not mentioned differently, 3-benzoyloxy-1,3,5(10)-estratriene-17β-[4-{p-(bis(2-chloroethyl)amino)phenyl}butanoyloxy]acetate was used as the present substance.

EXAMPLE 1

Study on an immunoreaction of the present substance in vitro.
(1) PHA reaction

PHA reaction was carried out to study the influence of the present substance on the blast formation reaction of the lymphocyte by PHA (phytohemagglutinin) which is the factor causing the nonspecific blast formation.

Human lymphocytes were separated from the peripheral blood by a specific gravity centrifugal precipitation method, etc. and washed 3 times with a phosphoric buffer solution. The separated lymphocytes were made to be a suspension containing $5 \times 10^5$ lymphocytes/ml while using RPMI 1640 (developed by Rosewell Park Memorial Institute, refer to J. A. M. A., 199, 519 (1967)).

After introducing 200 μl of the prepared suspension of the lymphocyte into each of the test wells, PHA and the present substance dissolved in DMSO at the concentration shown in Table 1 were also introduced into each of the test wells.

Thereafter, the treated lymphocytes were cultured for 3 days in a carbon dioxide culture box (kept at 37° C. and containing a mixture of 5% of $CO_2$ and 95% of air).

Then, $^3H$-thymidine was added to each of the test wells so that the final concentration thereof became 1 μci/ml, and after further culturing the lymphocytes for 24 hours, the cells which has taken $^3H$-thymidine were collected on a glass fiber filter with an autocell harvester and the radioactivity of the collected lymphocytes was measured. The results are shown in Table 1.

(2) Mixed lymphocyte culture (MLC) reaction

A suspension liquid of total lymphocytes separated from the blood of a person (A) were subjected to radiation treatment and the liquid was diluted with RPMI 1640 so that the liquid contained $5 \times 10^5$ cells/ml and was named as A.

Separately, a suspension liquid of total lymphocytes separated from the blood of another person (B) were diluted with RPMI 1640 so that the liquid contained $5 \times 10^5$ cells/ml and was named as B.

Into each of the test wells, each 100 μl of the suspension liquids A and B were introduced and after adding a solution of the present substance in DMSO at a concentration shown in Table 1 to each of the test wells, the lymphocytes in each well were incubated for 7 days in carbon dioxide. $^3H$-thymidine was added to each of the test wells in an amount of 0.25 μci before about 12 to 16 hours of the harvest.

The cultured lymphocytes were collected on glass fiber filters by a cell harvester and the radioactivity of the lymphocytes was measured. The results are shown in Table 1.

TABLE 1

The Effect of the Present Substance on PHA and MLC Reactions.

| Present substance (KM 2210) (μg/ml) | PHA reaction (%)* | MLC reaction (%)* |
|---|---|---|
| 0 (Control) | 100 | 100 |
| 25 | 59.9 | 7.3 |
| 50 | 87.3 | 10.2 |
| 100 | 75.7 | 7.2 |
| 200 | 66.4 | 2.2 |

In PHA reaction, no large difference of the amount of $^3H$-thymidine taken into the lymphocyte was observed between control and each concentration (25, 50, 100 and 200 μg/ml) of the present substance (it is deemed that there is no significant difference unless the percentage is less than 50). On the other hand, in MLC reaction, the remarkable reduction of the amount of $^3H$-thymidine taken into the lymphocytes was observed at each concentration of the present substance.

The fact suggests that the present substance has a strong suppressing activity selectively on the reaction which is specific to the isoantigen. Accordingly, it can be gathered from the fact that the present substance is particularly useful when the isoantigen becomes a problem, that is, in the suppression of the immunoreaction in such a case of transplantation of organs.

EXAMPLE 2

Bone-marrow transplantation experiment using mouse.

The effect of the present substance on the reaction to the isoantigen was studied.

The bone-marrow cells and the spleen cells from a male C3H/He mouse (age of 10 weeks and body weight of 25 to 30 g) were collected in RPMI 1640 containing 10% of FBS. The bone-marrow cells and the spleen cells were mixed together in the ratio 1:1 and a liquid suspension of the cells was prepared in the concentration of $8 \times 10^6$ cells/ml.

Separately, a group of male B6C3F$_1$ mouse (age of 10 weeks, body weight of 23 to 29 g, 6 mice/group) was exposed to a radiation of 900 rad and on the same day, the mixed liquid suspension was administered to each of the exposed mice from the caudal vein of the mouse at a dose of 0.5 ml/mouse.

After dispersing the present substance in a 0.5% suspension of methylcellulose in an aqueous physiological saline solution, the prepared suspension was orally administered to each of the inoculated mouse at a dose of 0 and 2 mg/kg/day, starting from the one day before the inoculation and every day thereafter, and the treated mice were observed on the life prolongation. The results are shown in Table 2.

TABLE 2

Life-Prolongation Effect of the Present Substance on the Mouse which was Exposed to Radiation and was Transplanted with the Bone-marrow Cells.

| Substance administered | Amount administered (mg/kg/day) | Number of animals (n) | Day of life-Prolongation (median value) |
|---|---|---|---|
| Control | 0 | 6 | 8 |
| Present Substance | 2 | 6 | >27 |

As are seen in Table 2, in the case of administering the present substance at the dose of 2 mg/kg, the median life-prolongation of more than 27 days were observed in contrast to only 8 days in the case of control and the life-prolongation effect of the present substance was clearly observed.

EXAMPLE 3

Preparation of medicinal composition.
(Recipe 1)

The following components were well mixed and pulverized and the pulverized composition was compressed to be tablets of 10 mm in diameter.

Recipe of the composition:

| | |
|---|---|
| Present substance | 40 parts by weight |
| Mannitol | 35 parts by weight |
| Sorbitol | 25 parts by weight |
| Carboxymethylcellulose | 5 parts by weight |

| | |
|---|---|
| Magnesium stearate | 5 parts by weight |
| Talc | 40 parts by weight |

(Recipe 2)

The following components were mixed well and the mixed composition was filled in the capsules No. 2 of Japanese Pharmacopoeia which had been colored by titanium oxide, according to the operation method for production of hard capsulated medicine of the general rule of medical preparation of the Japanese Pharmacopoeia, and prepared the hard capsule medicine.

Recipe of the composition:

| | |
|---|---|
| Present substance | 50 parts by weight |
| Potato starch | proper amount |
| Corn starch | 23 parts by weight |
| Crystalline cellulose | 46.5 parts by weight |
| Light silicic anhydride | 5.5 parts by weight |
| Talc | 18 parts by weight. |

What is claimed is:

1. A method of treating a patient for the purpose of suppressing immuno response of the patient, which comprises administering to the patient a pharmaceutically effective amount to suppress immuno response of said patient of an estradiol derivative represented by the formula (I):

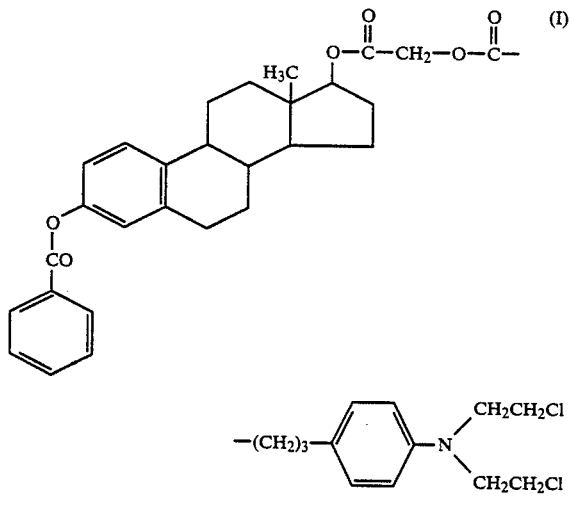

2. The method according to claim 1, wherein said estradiol derivative is 3-benzoyloxy-1,3,5(10)-estratriene-17β-[4-{p-(bis(2-chloroethyl)amino)phenyl}butanoyloxy]acetate.

3. The method according to claim 1, wherein said patient is scheduled to have an operation for the transplantation of bone marrow kidney, skin or heart.

4. The method according to claim 1, wherein said patient is suffering from kidney failures, thyroid gland diseases, chronic articular rheumatism, thrombocytopenia, systemic lupus erythematosus, myasthenia gravis, hepatitis, autoimmune diseases or multiple myositis.

5. A method of treating a patient for the purpose of suppressing immuno response of the patient, which comprises administering to the patient a pharmaceutically effective amount to suppress immuno response of said patient of a composition which contains an estradiol derivative represented by the formula (I), as an active ingredient:

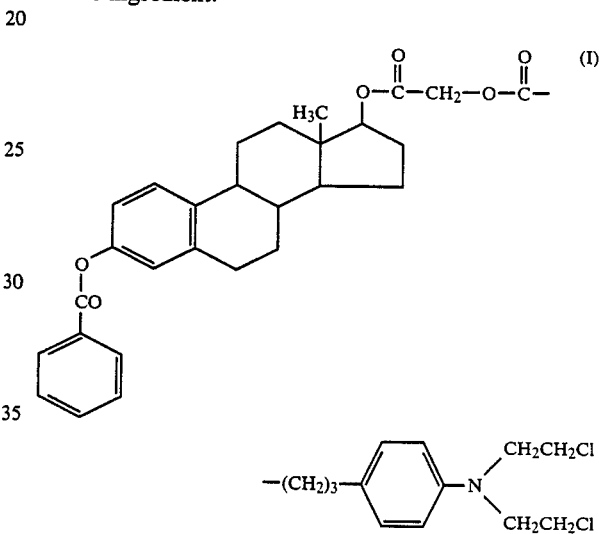

starch, crystalline cellulose, light silicic anhydride and talc and is encapsulated.

6. The method according to claim 5, wherein said estradiol derivative is 3-benzoyloxy-1,3,5(10)-estratriene-17β-[4-{p-(bis(2-chloroethyl)amino)phenyl}butanoyloxy]acetate.

7. The method of treating a patient according to claim 5, wherein said patient is scheduled to have an operation for the transplantation of bone marrow, kidney, skin or heart.

* * * * *

UNITED STATES PATENT AND TRADEMARK OFFICE
CERTIFICATE OF CORRECTION

PATENT NO. : 4,885,290
DATED : Dec. 5, 1989
INVENTOR(S) : Kiro Asano, et al

It is certified that error appears in the above-identified patent and that said Letters Patent is hereby corrected as shown below:

Title page:

The 4th inventor's last name is incorrectly recorded "Suzuki Toichi" should be:

--Yoichi Suzuki--

Signed and Sealed this

Nineteenth Day of February, 1991

*Attest:*

HARRY F. MANBECK, JR.

*Attesting Officer*     *Commissioner of Patents and Trademarks*